US012753410B2

(12) United States Patent
Zhang et al.

(10) Patent No.: US 12,753,410 B2
(45) Date of Patent: Oct. 6, 2026

(54) FATS AS A TARGET FOR TREATING TUMORS AND USES THEREOF

(71) Applicant: TIANJIN MEDICAL UNIVERSITY, Tianjin (CN)

(72) Inventors: Rongxin Zhang, Tianjin (CN); Kai Zhang, Tianjin (CN); Lijuan Zhang, Tianjin (CN); Zhenyi Xue, Tianjin (CN); Yan Li, Tianjin (CN)

(73) Assignee: TIANJIN MEDICAL UNIVERSITY, Tianjin (CN)

( * ) Notice: Subject to any disclaimer, the term of this patent is extended or adjusted under 35 U.S.C. 154(b) by 703 days.

(21) Appl. No.: 18/304,394

(22) Filed: Apr. 21, 2023

(65) Prior Publication Data

US 2023/0365973 A1 Nov. 16, 2023

Related U.S. Application Data

(63) Continuation-in-part of application No. 16/134,983, filed on Sep. 19, 2018, now abandoned, and a continuation of application No. PCT/CN2017/082989, filed on May 4, 2017.

(30) Foreign Application Priority Data

May 12, 2016 (CN) ......................... 201610315637.9

(51) Int. Cl.

| | |
|---|---|
| ***C12N 15/113*** | (2010.01) |
| ***A61K 35/15*** | (2025.01) |
| ***A61P 35/00*** | (2006.01) |

(52) U.S. Cl.

CPC .......... *C12N 15/1135* (2013.01); *A61K 35/15* (2013.01); *A61P 35/00* (2018.01); *C12N 2310/14* (2013.01)

(58) Field of Classification Search

CPC .............. C12N 15/1135; C12N 15/113; C12N 2310/14; A61P 35/00

See application file for complete search history.

(56) References Cited

U.S. PATENT DOCUMENTS

| | | | |
|---|---|---|---|
| 2008/0070254 A1 | 3/2008 | Coignet | |
| 2012/0196755 A1 | 8/2012 | Brewer et al. | |

FOREIGN PATENT DOCUMENTS

| | | |
|---|---|---|
| CN | 101798572 A | 8/2010 |
| CN | 101835902 A | 9/2010 |
| CN | 105963699 A | 9/2016 |

OTHER PUBLICATIONS

Zhang L, Zhang K, Zhang J, Zhu J, Xi Q, Wang H, Zhang Z, Cheng Y, Yang G, Liu H, Guo X, Zhou D, Xue Z, Li Y, Zhang Q, Da Y, Liu L, Yin Z, Yao Z, Zhang R. Loss of fragile site-associated tumor suppressor promotes antitumor immunity via macrophage polarization. Nat Commun. Jul. 14, 2021;12(1):4300. (Year: 2021).*

NCBI Reference Sequence: NM_001199941.1 (Year: 2010).*

Xifeng Zhang et al., "FATS is a transcriptional target of p53 and associated with antitumor activity", Molecular Cancer, 2010, 9:244, 7 pages.

Jun Zhang et al., "Expression and Clinical Significance of FATS in Human Breast Cancer Tissue", Chinese Journal of Clinical Oncology, vol. 38, issue No. 9, Dec. 31, 2011, p. 508 Conclusion.

Li et al., "An HDAC1-binding domain within FATS bridges p21 turnover to radiation-induced tumorigenesis", Oncogene (2010) 29, pp. 2659-2671.

Jun Zhang et al., "The value of FATS expression in predicting sensitivity to radiotherapy in breast cancer", Oncotarget (Mar. 2017), vol. 8, (No. 24), pp. 38491-38500.

Zheng Li et al., "Study on the oncogenic function of FATS, a new gene of chromosomal fragile locus", Proceedings of the 5th China Oncology Conference and the 7th Cross-Straits Oncology Conference, the International Society for Tumor Cell and Gene Therapy Conference, and the 2nd China-Japan Interventional Cancer Therapy Conference, 2008, Conclusion.

* cited by examiner

*Primary Examiner* — Fereydoun G Sajjadi
*Assistant Examiner* — Qinhua Gu

(57) ABSTRACT

A composition including modified macrophages and its use in the treatment of melanoma and pancreatic cancer. The modified macrophages have a deletion of fragile-site associated tumor suppressor (FATS) or include a small interfering RNA (siRNA) capable of silencing the FATS. The knockout or inhibition of FATS may promote the polarization of M0 macrophages into M1 macrophages and suppress the polarization of M0 macrophages into M2 macrophages. The FATS can be used as a target for the production of medications for the treatment of cancer or tumors.

16 Claims, 18 Drawing Sheets

Specification includes a Sequence Listing.

SEQUENCE LISTING

```
Sequence total quantity: 12
SEQ ID NO: 1            moltype = DNA  length = 2076
FEATURE                 Location/Qualifiers
source                  1..2076
                        mol_type = other DNA
                        note = Artificial sequence
                        organism = synthetic construct
SEQUENCE: 1
atgattaaac tgtctgggga aggattactg cacacgtgct atagtacaaa tgatcaaatc  60
gcccttaaaa acctgcagtc tgatgttaca gagaggaagt tggacttctc caaggagaca  120
ctggcatcac agaacacaag aatgatatca cctgtggtca tttcccggct gattgatgaa  180
aagaaatcta tggaaaatgg agcaatattg ccacaagcca ttgctcagcc tcagctgtgt  240
cccacaaagc cagctttggc caggcgcgat ggagtgagca tgcacaggcg atttgcttta  300
tctccagaca gactgggaat tttgactcca tcagatgatc aaggactgga gacagaaccg  360
ctgtctacag gggacaatct aggcaaaggt tcccacagcg gtttctcgtc tatcaccatt  420
actgcccgac gtgtgggccc tccagccagc agcttggtat gggacacttt tagggaccca  480
ctgtgtccca agtgcaaagc caaggatgct ctgttccaag agcccccagt tctggctggt  540
gatgcccatc tctgtcagca caatagaccc ttcacctgta cagagtcccc cagcaatggc  600
tccgtagagg ggatgaaggt tttccaggct cactcaaggc tgagtgcaag gcaggactac  660
tgggtcaccc acacgaatga caatgaggac agtttttctt cagacaattc accatcgaga  720
aaagtcccac tggtgttcag ttcttgtgtc cacttccggg tgtctcagca gtgtcccaat  780
gccatttact atttggacaa gtctctttct gttccccttg agcgacctca aattgctagc  840
cccaaaatgc acaggtctgt cctgtctctc agcctccgct gtagttccca ccagttaaca  900
gcagatggag tagacagctc agctaatgga gagccaatca gcacagctct atcacaggaa  960
ctctcggagg gaaagcagga cctcctaggt ccacaatggg gccagccaca aggtggtcac  1020
tggaaggaga gcccagcatt ggtgccagta catttgggga gtggcacatg ccctcggact  1080
ggctcccctc cactggaaaa tgtcaaattt gcagacgtgg gaaggaacca ggtcccagta  1140
cgaaaggaga aagaggacca tgcaacatgt accagtagca gccacaccaa ccaactctcc  1200
atccatattc ccggctggag ttacagggct gaaacaaaag tactttctgg aagcaagaag  1260
cagcagcaag aagcacaaag aactcttcct gctttcccag tgggacagaa gaccattaaa  1320
cacttccctc ctgaagggga cagttcacca agcagtgatg gtcaacctag catcctttca  1380
gagtccaatg agaggcaaca cccatacttc atgataccca gagtccctct gcctgggttt  1440
tattgccctt tacaaactgg gtgtgcctct ctgcaggaag atggtgctgt tcagatagaa  1500
acacacttcc ccaaagatta cacgtgctgt gacttggttg taaaactaaa ggaatgtgag  1560
aagaacgaag accccactgt cacccctgag ccctcaccag caaccccctc tccatcaacc  1620
ccagagggag cacagagctc tgacccatca gaagatagtt acgagcctct gctggcaagt  1680
tctatgactt tgcaggaagc actggaagtc catagacctc agttcatttc tcgctcacaa  1740
gaacggctgc aaaagcttaa gcgcatggta cagcaaagga aaacccaaca aaaggagagc  1800
ctggggcaga agcagagcct acttcctgtc cgcgccaaca agaagcagtt caccattccc  1860
catcctctta gtgataactt gttcaaaccc aaagaaagat gcatttcaga gaaggagatg  1920
catatgagat ctaaaagaat ctataataat ttgccggaag ttaaaaagaa aaaagaagag  1980
cagaagaaaa gaatgatctt acagagtaac cggctccgag cagaagtctt caaaaagcaa  2040
ttactggacc agctccttca aaggaatgca gtttga                            2076

SEQ ID NO: 2            moltype = DNA  length = 19
FEATURE                 Location/Qualifiers
source                  1..19
```

```
                         mol_type = other DNA
                         note = Aritificial sequence
                         organism = synthetic construct
SEQUENCE: 2
gcaacatgta ccagtagca                                                    19

SEQ ID NO: 3             moltype = DNA  length = 19
FEATURE                  Location/Qualifiers
source                   1..19
                         mol_type = other DNA
                         note = Artificial sequence
                         organism = synthetic construct
SEQUENCE: 3
acagagttct ccagaaaca                                                    19

SEQ ID NO: 4             moltype = DNA  length = 19
FEATURE                  Location/Qualifiers
source                   1..19
                         mol_type = other DNA
                         note = Artificial sequence
                         organism = synthetic construct
SEQUENCE: 4
gcagagggtt tgcatccat                                                    19

SEQ ID NO: 5             moltype = DNA  length = 19
FEATURE                  Location/Qualifiers
source                   1..19
                         mol_type = other DNA
                         note = Aritificial sequence
                         organism = synthetic construct
SEQUENCE: 5
gcaagtactg ggtcaccca                                                    19

SEQ ID NO: 6             moltype = DNA  length = 19
FEATURE                  Location/Qualifiers
source                   1..19
                         mol_type = other DNA
                         note = Artificial sequence
                         organism = synthetic construct
SEQUENCE: 6
gaaagtcact tgaaggaaa                                                    19

SEQ ID NO: 7             moltype = DNA  length = 19
FEATURE                  Location/Qualifiers
source                   1..19
                         mol_type = other DNA
                         note = Artificial sequence
                         organism = synthetic construct
SEQUENCE: 7
ggcaaatgtg ggagctaac                                                    19

SEQ ID NO: 8             moltype = DNA  length = 19
FEATURE                  Location/Qualifiers
source                   1..19
                         mol_type = other DNA
                         note = Artificial sequence
                         organism = synthetic construct
SEQUENCE: 8
cagtgtccag attcaatct                                                    19

SEQ ID NO: 9             moltype = DNA  length = 19
FEATURE                  Location/Qualifiers
source                   1..19
                         mol_type = other DNA
                         note = Artificial sequence
                         organism = synthetic construct
SEQUENCE: 9
ggagaccagg acctcgtag                                                    19

SEQ ID NO: 10            moltype = DNA  length = 19
FEATURE                  Location/Qualifiers
source                   1..19
                         mol_type = other DNA
                         note = Artificial sequence
                         organism = synthetic construct
SEQUENCE: 10
cagcgatcat gccaaccaa                                                    19

SEQ ID NO: 11            moltype = DNA  length = 19
```

-continued

```
FEATURE                 Location/Qualifiers
source                  1..19
                        mol_type = other DNA
                        note = Artificial sequence
                        organism = synthetic construct
SEQUENCE: 11
gcagcggagt caacattca                                        19

SEQ ID NO: 12           moltype = DNA  length = 19
FEATURE                 Location/Qualifiers
source                  1..19
                        mol_type = other DNA
                        note = Artificial sequence
                        organism = synthetic construct
SEQUENCE: 12
ggcaccgtca gatgagcga                                        19
```

FATS AS A TARGET FOR TREATING TUMORS AND USES THEREOF

CROSS-REFERENCE TO RELATED APPLICATIONS

This application is a continuation-in-part of application Ser. No. 16/134,983, filed on Sep. 19, 2018, now pending, which is a continuation of International Application Serial No. PCT/CN2017/082989, filed on May 4, 2017, and further claims priority of Chinese Patent Application No. 201610315637.9, filed on May 12, 2016. The content of the aforementioned application, including any intervening amendments thereto, is incorporated herein by reference.

REFERENCE TO AN ELECTRONIC SEQUENCE LISTING

The contents of the electronic sequence listing (WK_SequenceListing.xml; Size: 15,866 bytes; and Date of Creation: Aug. 1, 2023) are herein incorporated by reference in its entirety.

TECHNICAL FIELD

This application generally relates to compositions and methods for the treatment of cancers or tumors. Specifically, this application relates to compounds and compositions using fragile site-associated tumor suppressor (FATS) as target for treatment of cancers or tumors.

BACKGROUND

As a malignant tumor originating from melanocytes, melanoma is the most aggressive tumor among all skin tumors. Cells that produce pigments may be derived from various tissues including skin, mucous membrane and conjunctiva in the body. Despite of decades of continuous development of many chemotherapy drugs and methods for treating malignant tumors, the survival rate of patients with metastatic melanoma has still not increased. There are about 73,870 cases suffering from melanoma in the U.S. in 2015. Although melanoma is not as common as other skin cancers, for example, basal cell carcinoma and squamous cell carcinoma, melanoma results in a high percentage of deaths in all skin cancers. According to the extent of tumor progression, there are significant differences in terms of the survival rate of melanoma patients. Patients in early stages only need surgical resection, however, the patients in metastatic stages have only 16.6% of 5-year survival rate.

Fortunately, the understanding of melanoma in recent years provides some useful information for clinical research. The development of powerful molecular diagnostic tools and approaches lead to the discovery of various mutation, amplification or deletion of genes during the growth and survival of tumors, as well as the sensitivity response to small molecule inhibitors. This enables the development of efficient signal-transduction target and immunotherapeutic target. The unfavorable prognosis has changed after the emergence of systemic therapy. Six drugs (Ipilimumab, Vemurafenib, Dabrafenib, Trametinib, etc.) have been approved by the U.S. Food and Drug Administration (FDA) since 2011, these drugs can be used to treat melanoma via 4 different mechanisms (inhibiting CTL-associated antibody inhibitors, BRAF, MEK and PD-1 receptor).

It is found that the carcinogenic BRAF mutations promote tumor growth in up to 50% of melanomas. Mutations in BRAF and other genes (e.g., KIT) provides various approaches to systemic therapy. Targeted treatments, including the use of BRAF and MEK inhibitors, have increased the overall survival rate of melanoma patients with BRAF V600 mutation. In the past 5 to 10 years, the treatment of melanoma is of great change due to the discovery of a new type of immunoregulatory factor. The inhibition of immunoregulatory checkpoints has greatly altered the situation of melanoma treatment. Inactivation of immunoregulatory checkpoints limits the immune response of T cells in melanoma, which is a target for immunotherapy of cancers. It is very important to succeed in treatments using Ipilimumab as immunoregulatory checkpoint inhibitor and anti-PD-1 antibodies and targeting CTLA-4 and PD-1/PD-L1.

Pancreatic cancer is one of the most common malignant tumors of the digestive system. Patients usually have advanced due to an extremely low diagnosis rate of early pancreatic cancer, and the prognosis remains undesirable. In recent years, the incidence of pancreatic cancer has increased significantly. Global statistics shows that the deaths caused by pancreatic cancer take the fifth place among all cancer-related deaths. Furthermore, conventional radiotherapy and chemotherapy barely works for pancreatic cancer. Therefore, there is a need to develop new therapies such as immunotherapy to improve the effect for clinical therapy of pancreatic cancer.

A large number of studies have shown that immunotherapy of tumors is an option for patients having advanced cancer. Currently, immunotherapy is capable of destroying tumor cells, and the functional level of immune system is closely related to the prognosis and clinical therapeutic effect of tumors. It has been found that targeting tumor microenvironment (TME) has become an important strategy for anti-tumor therapies. It is known that immune cells in TME can affect the occurrence, development and invasion of tumors, as well as the final therapeutic effect.

Chromosomal fragile site is an unstable site-specific region in normal genome, including 88 common fragile sites (CFSs) and 39 rare fragile sites. CFSs are normal structures as the components of chromosome. In the case of replication abnormalities in the metaphase of cell division, the chromosomal fragile site fragile sites in the chromosome are most prone to cracks or breakpoints. CFSs are highly conserved during evolution. C10orf90 is a general fragile site established recently. It is found in initial studies that tumor suppression occurs upon over-expression of C10orf90 in several tumor cell lines and thus C10orf90 is named Fragile site-associated tumor suppressor (FATS). It has been reported that CFSs are also associated with immunity. Nevertheless, there is no report on the role of FATS in tumor immunity, considering that research on FATS are very limited.

SUMMARY

The present invention provides compositions using fragile site-associated tumor suppressor (FATS) as target for the treatment of cancers or tumors.

In an aspect, the present invention provides a composition comprising modified macrophages.

In some embodiments, the modified macrophages have a deletion of fragile-site associated tumor suppressor (FATS) of SEQ ID NO: 1.

In some embodiments, the modified macrophages comprise a small interfering RNA (siRNA) capable of silencing the FATS of SEQ ID NO: 1.

In some embodiments, the siRNA is selected from the group consisting of SEQ ID NOS: 2 to 12.

In some embodiments, the siRNA may be SEQ ID NO: 2, SEQ ID NO: 7, SEQ ID NO: 9, SEQ ID NO: 10 or SEQ ID NO: 11.

In some embodiments, the siRNA may be SEQ ID NO: 2 or SEQ ID NO: 10.

In some embodiment, the macrophages are bone marrow-derived macrophages (BMDMs). The macrophages may be M0 or M1 macrophages.

In some embodiments, the macrophages may be derived from an animal selected from the group consisting of a primate, a rodent and a pig.

In another aspect, the present invention provides a use of the composition comprising modified macrophages in the treatment of a tumor or cancer. In some embodiments, the tumor or cancer may be melanoma or pancreatic cancer.

In some embodiments, the present invention provides a method for treating melanoma in a subject, comprising administering a therapeutically effective amount of the composition into the subject in need thereof, thereby treating the melanoma.

In some embodiments, the present invention provides a method for treating melanoma in a subject, comprising: a) introducing a small interfering RNA (siRNA) capable of silencing fragile-site associated tumor suppressor (FATS) of SEQ ID NO: 1 into macrophages to produce modified macrophages, wherein the siRNA is selected from the group consisting of SEQ ID NOS: 2 to 12; and b) administering a therapeutically effective amount of a composition comprising the modified macrophages into the subject in need thereof, thereby treating the melanoma. The siRNA may be introduced into the macrophages by transfection, typically using a transfection reagent.

In some embodiments, the composition comprising the modified macrophages may be administered via injection.

In another aspect, the present invention provides a method for treating pancreatic cancer in a subject, comprising:

administering a therapeutically effective amount of the composition into the subject in need thereof, thereby treating the pancreatic cancer.

The FATS can be used as a target to design the composition for treating cancers, for example, melanoma and pancreatic cancer. The composition according to the present invention may promote polarization of M0 macrophages into M1 macrophages and/or inhibits polarization of M0 macrophages into M2 macrophages.

BRIEF DESCRIPTION OF DRAWINGS

FIG. 1A is a typical flow cytometry plot showing the frequency of M1 macrophages after the polarization of M0 macrophages into M1 macrophages. FIG. 1B is a statistical chart showing the frequency of M1 macrophages after the polarization.

FIG. 1C is a typical flow cytometry plot showing the frequency of M2 macrophages after the polarization of M0 macrophages into M2 macrophages. FIG. 1D is a statistical chart showing the frequency of M2 macrophages after the polarization (, $P<0.01$; *, $P<0.001$).

FIG. 4A is a typical flow cytometry showing the frequency of early apoptotic M2 macrophages. FIG. 4B is a statistical chart showing the frequency of early apoptotic M2 macrophages. FIG. 4C shows the expression level (protein) of Cleaved-caspase3 and Bcl2 (both as apoptosis signal) in M2 macrophages (**, $P<0.01$).

FIG. 6A shows a growth curve of melanoma after the adoptive infusion of BMDMs of the WT and KO mice into the C57BL/6 mice. FIG. 6B is an image showing a representative result of the melanoma size after the adoptive infusion of BMDMs of the WT and KO mice into the C57BL/6 mice. FIG. 6C shows a final weight of tumor after the adoptive infusion of BMDMs of the WT and KO mice into the C57BL/6 mice (*, P<0.05; ***, P<0.001).

FIG. 7A shows the expression level (mRNA) of FATS in macrophages detected by RT-PCR after a 24-hour transfection with FATS-siRNA (SEQ ID NO: 2)/NC-siRNA (****, P<0.0001). FIG. 7B shows the expression level (mRNA) of FATS in macrophages detected by RT-PCR after a 24-hour transfection with FATS-siRNAs (i.e., si-1-10 represented by SEQ ID NOS: 3-12)/NC-siRNA (*, P<0.05; , P<0.01; *, P<0.001;**, P<0.0001). FIG. 7C shows a growth curve of melanoma in the WT and KO mice with siRNA infusion, respectively (*, P<0.001).

DETAILED DESCRIPTION OF EMBODIMENTS

Figure 1A:
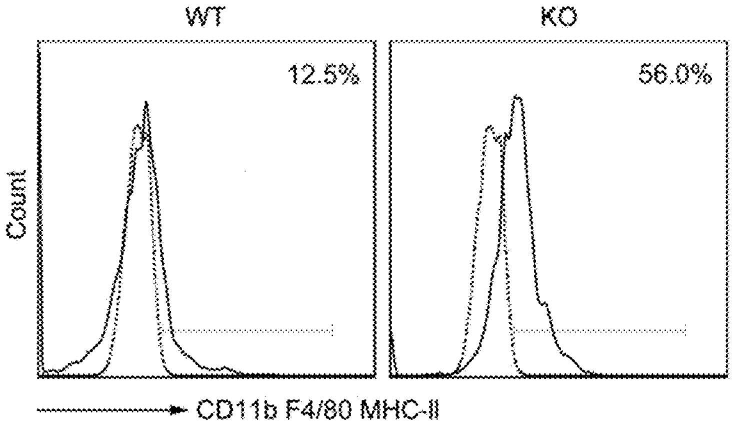
FIGS. 1A-D show that FATS defect promotes the polarization of macrophages to M1 macrophages and inhibits the polarization of macrophages to M2 macrophages. Bone marrow cells were separated from the WT and KO mice, and added with macrophage colony-stimulating factor (M-CSF) for directed differentiation into M0 macrophages. The M0 macrophages were then added with IFN-γ and LPS, or IL-4 to polarize into M1 or M2 macrophages, and the macrophages were collected 16 hours later, and were analyzed by flow cytometry for detecting the frequency of M1 and M2 macrophages.

Before the present compositions and methods are described, it is to be understood that this invention is not limited to particular compositions, methods and experimental conditions described below.

Definitions

Various terms used throughout this specification shall have the definitions set out herein.

As used herein, the singular forms "a", "an" and "the" includes plural references unless indicated otherwise.

As used herein, the term "A", "T", "C", "G" and "U" refer to adenine, thymine, cytosine, guanine, uracil as a nucleotide base, respectively.

As used herein, the term "siRNA" refers to a small interfering RNA. RNA interference refers to the process of sequence-specific post-transcriptional gene silencing in a cell or an animal mediated by short interfering RNA.

As used herein, the term "FATS-siRNA" or "FATS-siRNAs" refers to siRNA capable of inhibiting or silencing fragile site-associated tumor suppressor (FATS) gene (SEQ ID NO: 1). As used herein, the terms "silencing" and "inhibiting", in as far as they refer to the FATS refers to at least partial suppression of the expression of the FATS.

As used herein, the term "deletion", "deficient" or "defect" in the context of FATS refers to the knock out of the FAST.

Macrophages are a type of white blood cell that play an important role in the human immune system and carry out various functions including engulfing and digesting microorganisms; clearing out debris and dead cells; and stimulating other cells involved in immune function. Macrophages confer innate immunity, which is typically the first line of defense against foreign antigens. Adaptive immunity, on the other hand, is the subtype of the immune system that involves specialized immune cells and antibodies. In addition to having an immune role, macrophages also secrete anti-inflammatory cytokines (i.e., small signaling proteins) and help mediate reparative processes. Macrophages form from monocytes, which themselves derive from the bone marrow. Macrophages can be found within many organs in the body, including the liver, brain, bones, and lungs, as well as in the blood, particularly at sites of infection.

As used herein, the terms "M0", "M1" and "M2" refer to different phenotypes of macrophages. M0 macrophages are a resting or non-activated state of macrophages before their polarization. M0 macrophages are unpolarized and can polarize into classically activated M1 or alternatively activated M2 phenotypes. M1 macrophages are classically activated, typically by IFN-γ or lipopolysaccharide (LPS), and produce proinflammatory cytokines, phagocytize microbes, and initiate an immune response. M1 macrophages produce nitric oxide (NO) or reactive oxygen intermediates (ROI). M2 macrophages are alternatively activated by exposure to certain cytokines such as IL-4, IL-10, or IL-13. M2 macrophages will produce either polyamines to induce proliferation or proline to induce collagen production.

As used herein, the term "therapeutically effective amount" refers to an amount that provides a therapeutic benefit in the treatment, prevention, or management of pathological processes of tumor or cancer, e.g., melanoma.

Transfection is the process of introducing nucleic acids into eukaryotic cells by nonviral methods. Cell transfection reagents are used to introduce foreign nucleic acids (such as DNA or RNA) into cells. Transfection reagents can vary depending on the type of cells being transfected, the type of nucleic acid being introduced, etc.

Common types of transfection reagents include lipid-based transfection reagents, polymer-based transfection reagents, calcium phosphate-based transfection reagents, electroporation-based transfection reagents. For example, lipid-based transfection reagents have low cytotoxicity, and can be used with a variety of cell types.

Unless defined otherwise, all technical and scientific terms used herein have the same meaning as commonly understood by one of skill in the art to which this invention belongs.

This application will be further described below in conjunction with preferred embodiments.

EXAMPLES

Example 1 Establishment of Mouse Melanoma Model

SPF-grade female C57BL/6 mice, aged 6-8 weeks and weighing 18-20 g, were purchased from Beijing Vital River Laboratory Animal Technology Co., Ltd. The mice were raised in a SPF-grade room of the Experimental Animal Center of Tianjin Medical University. The ambient temperature of the room was maintained at 20-25° C., and the relative humidity (RH) is maintained at 40%-60%.

B16 cells (murine melanoma cells) were cultured in a DMEM medium containing 10% fetal bovine serum (FBS) and 1% double antibody to a logarithmic phase of the cells. The cells were trypsinized, collected, centrifuged, and washed twice with phosphate buffered saline (PBS). The cells were counted, and the cell concentration was adjusted to $2\times10^6$/mL. Each mouse was injected with 100 μL of the cell suspension, i.e., $2\times10^5$ cells per mouse. The tumor growth of the mice was observed every other day, and the length and width of the tumor were measured with a vernier caliper and recorded.

Example 2 Isolation of Mouse Bone Marrow-Derived Macrophages

Female FATS-deficient C57BL/6 mice, aged 6-8 weeks and weighing 18-20 g, were provided by Tianjin Medical University Cancer Institute & Hospital. Wild-type SPF-grade female C57BL/6 mice, aged 6-8 weeks and weighing 18-20 g, were purchased from Beijing Vital River Laboratory Animal Technology Co., Ltd. The mice were all raised in a SPF-grade room of the Experimental Animal Center of Tianjin Medical University, with the ambient temperature maintained at 20-25° C., and relative humidity (RH) at 40%-60%. The wild-type mice were used as control.

A buffer for cell sorting was prepared from 10% bovine serum albumin (BSA) by 20-fold dilution with 1×PBS (0.5% BSA/PBS). The cell sorting buffer was stored at 4° C. for use.

The FATS-deficient mice were anaesthetized and sacrificed by cervical dislocation. Bilateral lower limbs were disinfected with 75% alcohol, and the femur and tibia were separated and immediately transferred to cold PBS. After removing the surface residual tissue, the femur and tibia were placed in a clean bench. Two ends of the femur were cut along the joint to expose the medullary cavity, and the bone marrow was flushed into a culture dish with 1×PBS by a 1 mL syringe, and washed repeatedly therewith until the tibia turned white. The bone marrow was blown into single cells with a 1 mL pipette, and the cell suspension was collected in a sterile 15 mL centrifuge tube and centrifuged at 1,000 rpm for 5 min. The supernatant was discarded, and the cells were suspended with 1×PBS and centrifuged at 1,000 rpm for 5 min. The supernatant was discarded, and the cells were resuspended with 1640 medium containing 10% FBS, such that bone marrow-derived (BM-derived) macrophages from FATS-deficient mice were isolated. Bone marrow-derived macrophages from wild-type mice were isolated following the treatment for FATS-deficient mice.

Example 3 Directed Differentiation of Mouse Bone Marrow-Derived Macrophages

A macrophage-stimulating factor (M-CSF, 10 ng/mL) was added to the BM-derived macrophages isolated from the FATS-deficient mice. The macrophages were cultured for 5 days to obtain M0 macrophages, during which half of the medium may be replaced on the 3$^{rd}$ day of the culture.

In accordance with the differentiation conditions of the bone marrow-derived macrophages from the FATS-deficient mice, the BM-derived M0 macrophages from the wild-type mice were obtained.

Example 4 Typing and Detection of Macrophages

Staining Blocking Buffer for Flow Cytometry

800 μL of 10% BSA was added with 200 μL of rat serum. They were mixed completely and stored at 4° C. in the dark.

Staining Buffer (SB) for Flow Cytometry 10 mL of FBS and 5 mL of 10% $NaN_3$ were added to 500 mL of PBS. They were fully mixed and stored at 4° C. for use.

4% paraformaldehyde 2 g paraformaldehyde was added to 45 mL ultra-pure water, to which 1 mol/L NaOH was then added. The mixture was kept at 56° C. overnight for complete dissolution. After cooled to room temperature, the mixture was added with 5 mL of 10×PBS, further added with 50 μL of 1 mol/L $CaCl_2$ and 50 μL 1 mol/L $MgCl_2$, adjusted to pH 7.3, and stored at 4° C. in the dark.

The cells to be tested were collected and centrifuged at 1500 rpm for 5 min. The supernatant was discarded, and the cells were resuspended with 1 mL of 1×PBS, and centrifuged at 1500 rpm for 5 min. The supernatant was discarded, and the cells were dispensed to a blank tube, a single-staining tube, an isotype control tube and a test tube, which were respectively added with 1×PBS till a volume of about 100 μL.

Blocking

Each tube was added with 25 μL of blocking buffer, and was kept at 4° C. in the dark for 30 min.

Surface Staining

Each tube was added with a rat anti-mouse fluorescent antibody, and the isotype tube was further added with a matching isotype anti-body according to the requirements to avoid false positive. The tubes were kept at 4° C. in the dark for 30 min, added with 1 mL of PBS, and centrifuged at 1500 rpm for 5 min. The cells were washed twice, added with 50-100 μL (each tube) of 4% paraformaldehyde or fixing buffer for fixation (can be stored for a short time at 4° C.), and then analyzed by flow cytometry.

M1 macrophages: CD11b-FITC/MHC-II-PE/F4/80-APC;

M2 macrophages: CD206-FITC/CD11b-PE/F4/80-APC.

We separated the bone marrow cells from WT and KO mice and added M-CSF for directed differentiation into macrophages. On the 5$^{th}$ day of differentiation, the cells were added with IFN-γ and LPS for polarization into M1 macrophages and IL-4 for polarization into M2 macrophages, respectively. The cells were collected 16 hours later, and were comprehensively analyzed for the effect of FATS defect on the polarization into M1 and M2 macrophages.

Figure 1B:
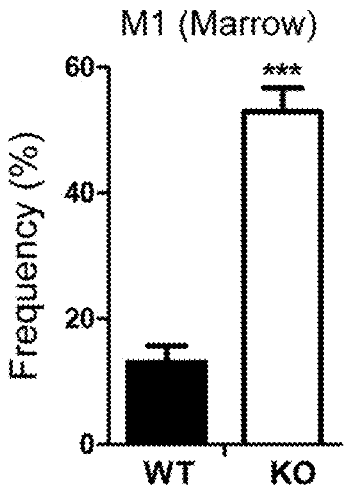
Figure 1C:
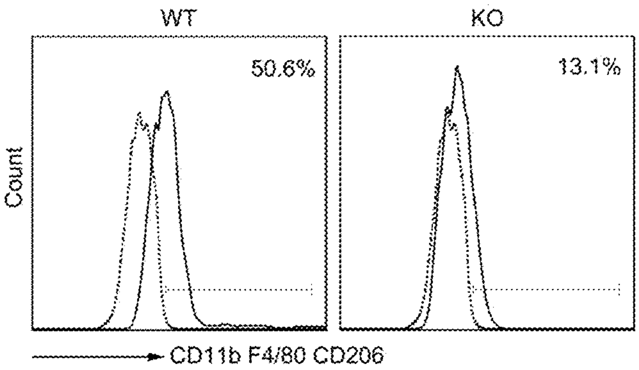
Figure 1D:
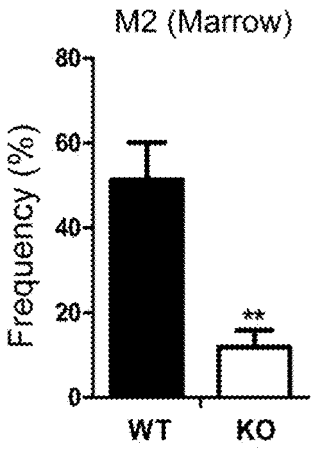

First, we detected and analyzed the frequency of M1 and M2 macrophages in WT and KO mice using flow cytometry. The result shows that under M1 polarization condition, the frequency of M1 macrophages in KO mice was much higher than that in WT mice (FIGS. 1A-B). Such result indicates that macrophages apparently tended to polarize into M1 macrophages upon FATS defect. Furthermore, the result also shows that under M2 polarization conditions, the frequency of M2 macrophages was significantly lower in KO mice than in WT mice (FIGS. 1C-D). Such result confirmed that FATS defect can directly regulate the macrophage polarization, and specifically it promoted the polarization into M1 macrophages and inhibited the polarization into M2 macrophages.

Figure 2:
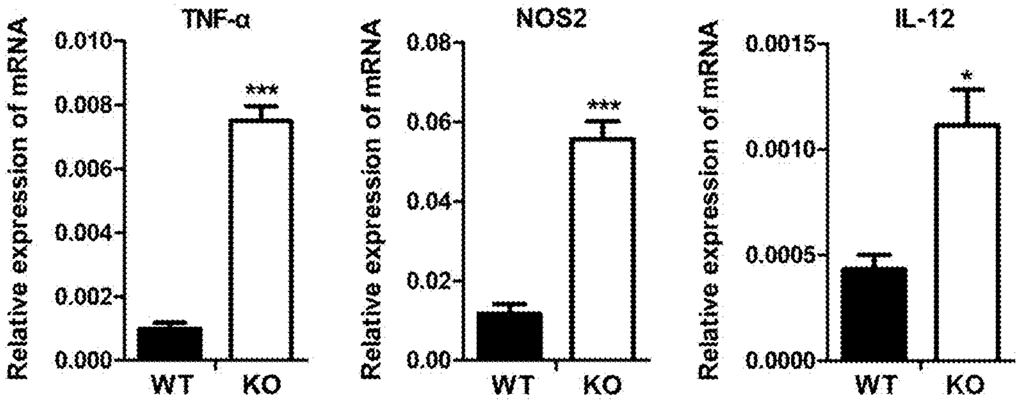
FIG. 2 shows that FATS defect promotes the gene expression of IL-12, TNF-α and NOS2 in M1 macrophages. Bone marrow cells were separated from the WT and KO mice, and added with M-CSF for directed differentiation into M0 macrophages. The M0 macrophages were then added with IFN-γ and LPS to polarize into M1 macrophages. The macrophages were collected to detect the expression of M1 macrophage-associated factors with real-time quantitative PCR. The figure is a statistical chart showing the gene expression (mRNA) level of TNF-α, NOS2 and IL-12 in M1 macrophages (*, $P<0.05$; , $P<0.01$; *, $P<0.001$).
Figure 3:
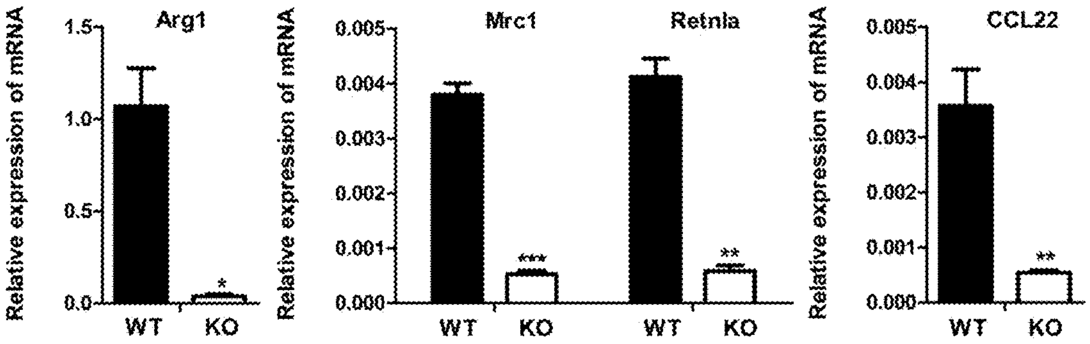
FIG. 3 shows that FATS defect inhibits the gene expression of Arg1, Mrc1, Retnla and CCL22 in M2 macrophages. Bone marrow cells were separated from the WT and KO mice, and added with M-CSF for directed differentiation into M0 macrophages. The M0 macrophages were then added with IL-4 to polarize into M2 macrophages. The macrophages were collected to detect the expression of M2 macrophage-associated factors with real-time quantitative PCR. This figure is a statistical chart showing the gene expression level (mRNA) of Arg1, Mrc1, Retnla and CCL22 in M2 macrophages (*, $P<0.05$; , $P<0.01$; *, $P<0.001$).

Meanwhile, we also detected the expression level of M1 and M2 macrophage-associated genes in WT and KO mice under different polarization conditions by RT-PCR. The result was consistent with that of the flow cytometry, that the mRNA level of IL-12, TNF-α and NOS2 in M1 macrophages was significantly higher in KO mice than in WT mice upon the polarization of M0 macrophages into M1 macrophages (FIG. 2). While upon the polarization into M2 macrophages, the mRNA level of cytokines expressed by M2 macrophages (Arg1, Mrc1, Retnla and CCL22) was significantly lower in KO mice than in WT mice (FIG. 3). These results indicate that FATS defect significantly promoted macrophage polarization into M1 macrophages, and at the same time inhibited the polarization into M2 macrophages.

Figure 4A:
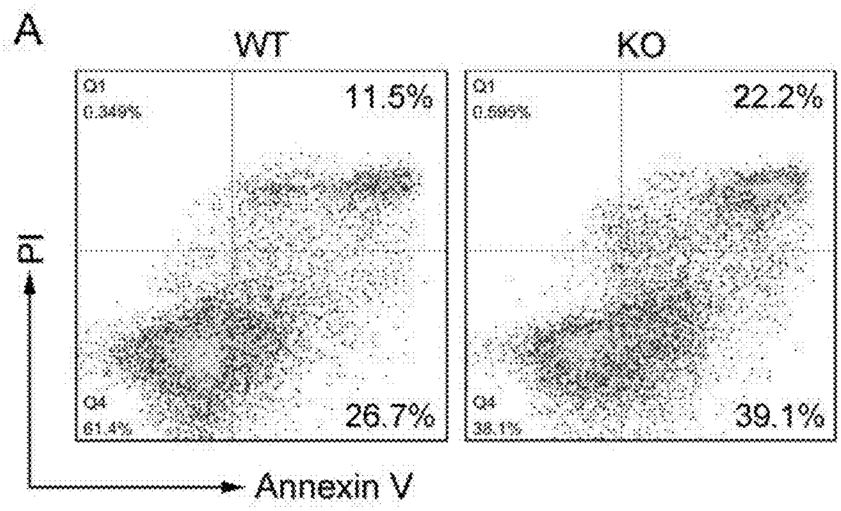
FIGS. 4A-C show that FATS defect promotes the apoptosis of M2 macrophages. Bone marrow cells were separated from the WT and KO mice, and added with M-CSF for directed differentiation into M0 macrophages. The M0 macrophages were then added with IL-4 to polarize into M2 macrophages. The macrophages were collected for an apoptosis kit assay to detect apoptosis of M2 macrophages and the expression of apoptosis-associated proteins by immunoblot.
Figure 4B:
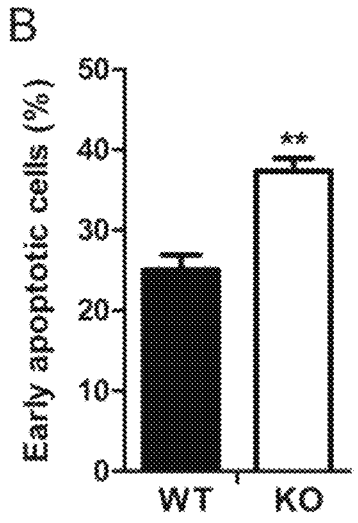
Figure 4C:
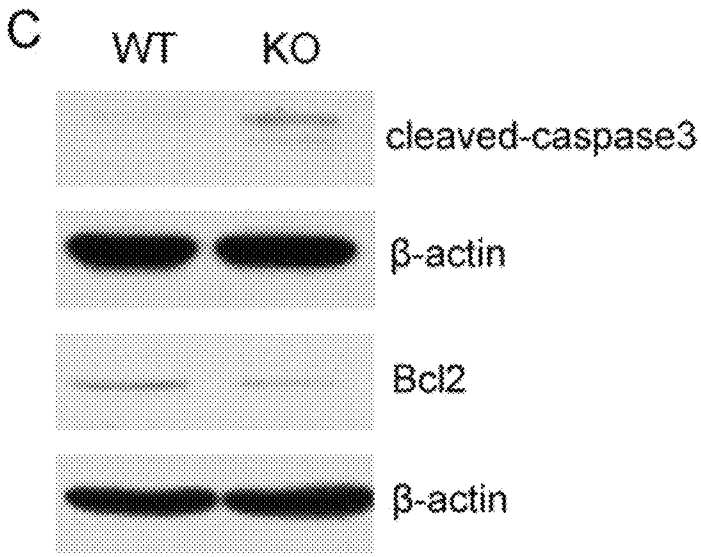

Immunoblot assays were performed on the collected M1 and M2 macrophages for the expression level of apoptosis-related signals. The result of flow cytometry showed a significant increase in cell apoptosis (in terms of both early and late apoptosis) during the polarization into M2 macrophages upon FATS defect (FIGS. 4A-B). Such result indicated that FATS defect promoted the apoptosis of M2 macrophages, which was a possible cause of the decrease in the frequency of M2 macrophages in KO mice. Moreover, we examined the expression of apoptosis-related signals in M2 macrophages from WT and KO mice. The expression level of Cleaved-caspase3 protein was increased in M2 macrophages from KO mice compared to that from WT mice. Meanwhile, the expression of apoptosis-suppressive Bcl2 protein was inhibited in the FATS-deficient macrophages (FIG. 4C). It is suggested that FATS defect promoted apoptosis in M2 macrophages, thereby reducing the frequency of M2 macrophages.

Figure 5:
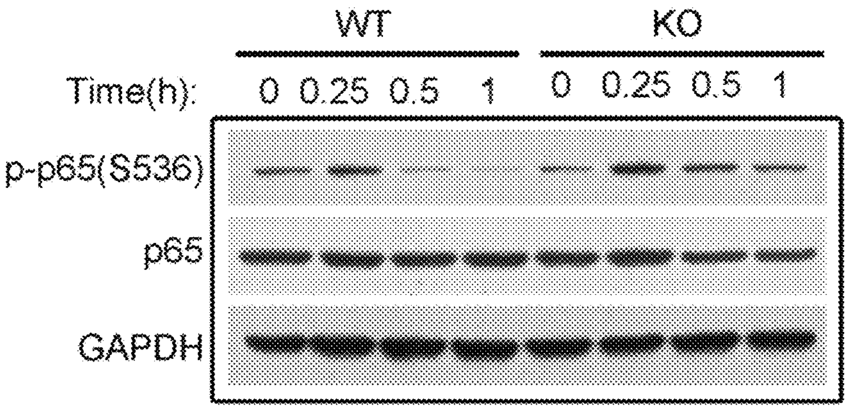
FIG. 5 shows that FATS defect activates NF-κB signaling pathway in macrophages. Bone marrow cells were separated from the WT and KO mice, and were added with M-CSF for directed differentiation into M0 macrophages. The macrophages obtained were stimulated with LPS to extract protein for a phosphorylation level detection of intracellular NF-κB signaling pathway at different time by immunoblot, indicating the activation level of the NF-κB signaling pathway.

To further investigate the mechanism by which FATS regulates macrophage polarization, we examined signaling pathways associated with macrophage polarization. The activity of NF-κB signaling pathway was examined during the polarization of bone marrow-derived macrophages into M1 macrophages. As shown in FIG. 5, p-p65 was significantly increased in the NF-κB signaling pathway upon FATS defect (FIG. 5). Such result indicated that FATS defect activated the NF-κB signaling pathway in macrophages and promoted the polarization of M0 macrophages into M1 macrophages, thereby increasing the frequency of M1 macrophages.

Example 5 Adoptive Therapy Using Bone Marrow-Derived Macrophages from FATS-Knock Out (FATS-KO) Mice The mice in Example 1 were randomly divided into two groups, one for the experimental group and the other for the control group, with five mice in each group. M0 macrophages differentiated from bone marrow cells from the FATS-KO mice (referring to Examples 2 and 3) were adoptively infused into the mice in the experimental group via tail vein injection on the $2^{nd}$ and $7^{th}$ day of the tumor grafting. Similarly, M0 macrophages differentiated from bone marrow cells from the wild-type mice (referring to Examples 2 and 3) were adoptively infused into the mice in the control group via tail vein injection on the $2^{nd}$ and $7^{th}$ day of the tumor grafting. The mice were stimulated with LPS for 12 h before the injection, and the tumor size was continuously monitored. The mice were sacrificed 16 days after the tumor grafting, and the tumor tissues were collected. The tumor was weighed, and the tumor volume was calculated by $V=(\text{length}\times\text{width}^2)/2$ ($mm^3$).

Figure 6A:
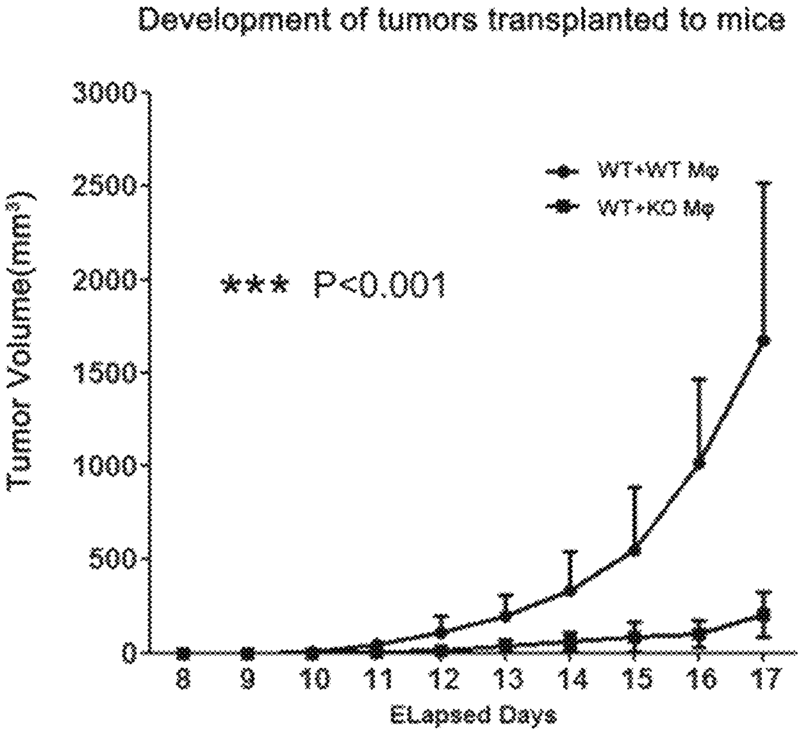
FIGS. 6A-C show that an adoptive therapy using bone marrow derived macrophages (BMDMs) with FATS deletion can be performed to significantly inhibit tumor growth. Ten female C57BL/6 mice, aged 6-8 weeks and weighing 18-20 g, were subcutaneously injected with B16 cells ($2\times10^5$/mouse) to build a mouse subcutaneous melanoma xenograft model. The mice were randomly divided into two groups (5 mice per group). M0 macrophages, derived from the directed differentiation of bone marrow cells (stimulated with LPS for 12 hours) of the WT and KO mice, were adoptively infused into the C57BL/6 mice on the $2^{nd}$ and $7^{th}$ day of tumor-graft experiment, respectively, and tumor size was continuously monitored. The C57BL/6 mice were sacrificed after 16 days of tumor-graft, and tumor tissue was separated for weighing and imaging.
Figure 6B:
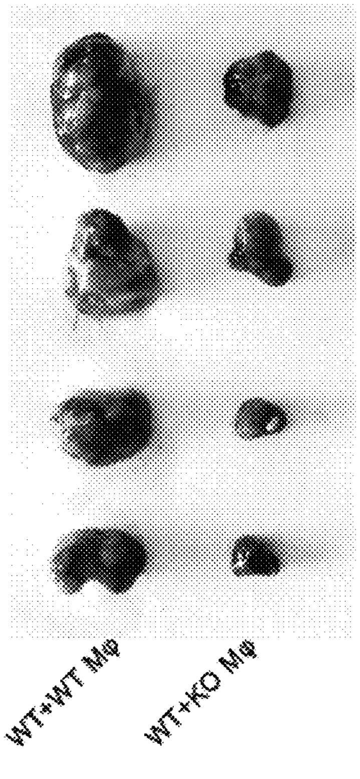
Figure 6C:
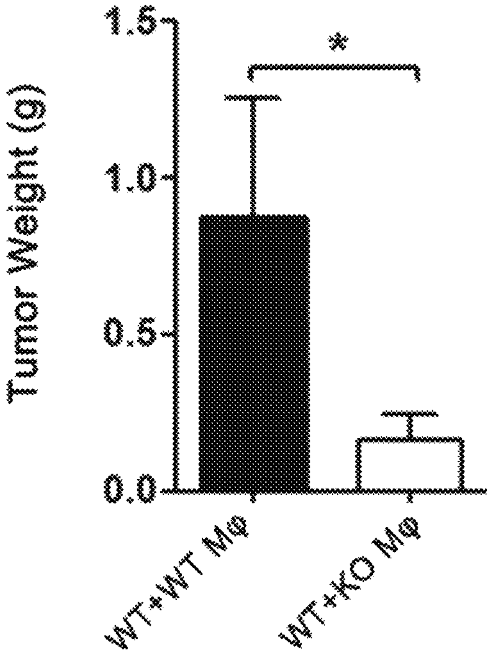

The results demonstrated that the macrophages from the FATS-deficient mice exhibited a strong killing ability in the tumor growth, and can inhibit the tumor growth and development. Through the adoptive therapy with the macrophages from the FATS-deficient mice, the growth of melanoma was significantly inhibited (FIG. 6A), and the final size of the tumor was significantly reduced (FIG. 6B), along with a significant decrease in tumor weight (FIG. 6C).

Example 6 Separation and Flow Cytometry of Mononuclear Cells from Tumor Tissue Tumor tissue was separated from the mice, and transferred to a clean bench. The tumor tissue was cut with a flat-head shear to small pieces of about 1 mm in diameter, which were digested with about 10 mL of a digestive enzyme (0.05 mg/mL collagenase IV+0.05 mg/mL hyaluronidase+0.05 mg/mL DNase I) at 37° C. for 1 h. After the digestion, the cells were transferred to a disposable cell sieve, and ground with the needle head of a 1 mL sterile syringe; meanwhile, 1×PBS was added to filter the ground fluid. The filtrate was collected in a 15 mL sterile centrifuge tube, and centrifuged at 1500 rpm for 5 min, where such operation was repeated once. The supernatant was discarded, and the cells were resuspended with 4 mL of sample diluent, and then added with an equal volume of a mouse lymphocyte separation medium. The cell fluid was centrifuged at 2,000 rpm at room temperature for 20 min, with the speed block and brake block both set to 0. The centrifuge tube was taken out smoothly, and the liquid above the white film-layer was sucked out with a 5 mL pipette, with 0.5 mL of liquid left above the white film-layer. Then the white-film layer was sucked out with a 200 μL pipette, placed in a 15 mL sterile centrifuge tube, added with 1×PBS in a volume ratio of 1:3, and centrifuged for 5 min for 3 times, respectively at 2000, 1800 and 1500 rpm. The supernatant was discarded, and the cells were resuspended in 1640 medium containing 10% FBS and 1% double antibody and cultured for later use. The proportion of macrophages in the tumor and the proportion of M2 macrophages were measured by flow cytometry.

Example 7 Introduction of FATS-siRNA into Bone Marrow-Derived Macrophages from Wild-Type (WT) Mice We used FATS-siRNAs designed for silencing the FATS or inhibiting the expression of the FATS for transfection. Specifically, the sequences of the FATS-siRNAs were as follows:

```
                                  (SEQ ID NO: 2)
GCAACATGTACCAGTAGCA;

                                  (SEQ ID NO: 3)
ACAGAGTTCTCCAGAAACA;

                                  (SEQ ID NO: 4)
GCAGAGGGTTTGCATCCAT;

                                  (SEQ ID NO: 5)
GCAAGTACTGGGTCACCCA;

                                  (SEQ ID NO: 6)
GAAAGTCACTTGAAGGAAA;

                                  (SEQ ID NO: 7)
GGCAAATGTGGGAGCTAAC;

                                  (SEQ ID NO: 8)
CAGTGTCCAGATTCAATCT;

                                  (SEQ ID NO: 9)
GGAGACCAGGACCTCGTAG;

                                 (SEQ ID NO: 10)
CAGCGATCATGCCAACCAA;

                                 (SEQ ID NO: 11)
GCAGCGGAGTCAACATTCA;

                                 (SEQ ID NO: 12)
GGCACCGTCAGATGAGCGA.
```

The WT mouse bone marrow-derived M0 macrophages collected in Example 3 were inoculated into a 12-well plate ($5\times10^6$ cells per well) till the cell confluence of 60-80%.

FATS-siRNA and Lipofectamine™ RNAiMAX Transfection Reagent each were diluted with RPMI1640 complete medium, according to dilution schemes in Table 1. The diluted FATS-siRNA and diluted Lipofectamine RNAiMAX Reagent were mixed in a volume ratio of 1:1. The mixture was stranded at room temperature for 5 min, and then co-incubated with the cells for 1-3 days. The transfection efficiency was detected under microscope. Quantitative PCR was performed 24 hours later to further detect the transfection efficiency.

TABLE 1

Dilution Scheme for FATS-siRNA and Lipofectamine ™ RNAiMAX Transfection Reagent

| Material/Reagent | 96-well plate | 24-well plate | 6-well plate |
|---|---|---|---|
| Adherent cells | (1-4) × $10^4$ | (0.5-2) × $10^5$ | (0.25-1) × $10^6$ |
| Medium for experiment | 25 μL | 50 μL | 150 μL |
| Lipofectamine ™ RNAiMAX Reagent | 1.5 μL | 3 μL | 9 μL |
| Medium for experiment | 25 μL | 50 μL | 150 μL |
| siRNA | 1.5 μL | 3 μL | 9 μL |
| Diluted FATS-siRNA | 25 μL | 50 μL | 150 μL |
| Diluted Lipofectamine ™ RNAiMAX Reagent | 25 μL | 50 μL | 150 μL |

TABLE 2

Preparation of siRNA-lipid mixture and cell transfection

| Material/Reagent | 96-well plate | 24-well plate | 6-well plate |
|---|---|---|---|
| siRNA-lipid mixture | 10 μL | 50 μL | 250 μL |
| Final concentration of siRNA | 1 pmol | 5 pmol | 25 pmol |
| Final concentration of Lipofectamine ™ RNAiMAX Reagent | 0.3 μL | 1.5 μL | 7.5 μL |

Example 8 Directed Differentiation of FATS-siRNA-Transfected Macrophages 24 hours after the FATS-siRNA transfection, LPS (1 μg/mL) was introduced to induce the polarization of M0 macrophages into M1 macrophages. 12 hours later, cells were collected and counted, and then adjusted to a concentration of $1\times10^7$ cells/mL. The cells were analyzed by flow cytometry to determine the macrophage phenotype. Notes: empty vector-macrophage may be used as control.

Example 9 Adoptive Therapy Using WT Mouse Bone Marrow-Derived Macrophages Transfected with FATS-siRNA The M1 macrophages obtained in Example 8 were adoptively infused into the tumor-bearing mice obtained in Example 1 by tail vein injection on the $1^{st}$ and $7^{th}$ day of the tumor bearing. The tumor size was monitored every other day. The mice were sacrificed 16 days later, and the tumor tissue was separated. The tumor volume and weight were measured.

Notes: macrophages transfected with NC-siRNA may be used as control.

It was demonstrated that the adoptive infusion of FATS-siRNA-transfected bone marrow-derived M1 macrophages can significantly inhibit the tumor growth.

Figure 7A:
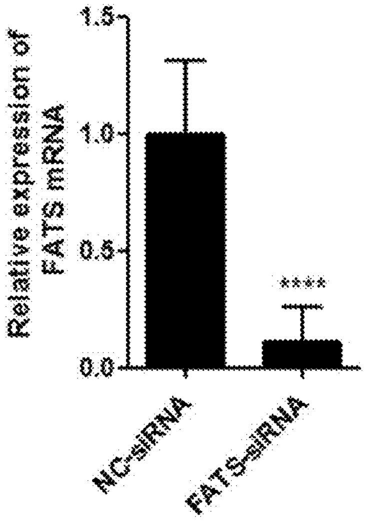
FIGS. 7A-C show that an adoptive infusion of BMDMs transfected with FATS-siRNAs can be performed to significantly inhibit tumor growth. Bone marrow cells were separated from WT mice, and added with M-CSF for directed differentiation into M0 macrophages. The M0 macrophages were then transfected with FATS-siRNAs and NC-siRNA, respectively. 24 hours later, the transfected macrophages were stimulated with LPS (1 μg/mL) for 12 hours. The stimulated cells were collected, with cell concentration adjusted to $1\times10^7$/ml, and were introduced into mice by a tail vein injection (100 μL per mouse). Such adoptive infusion of the transfected macrophages was performed on the $2^{nd}$ and $7^{th}$ day of tumor-graft, and tumor growth was continuously monitored.
Figure 7B:
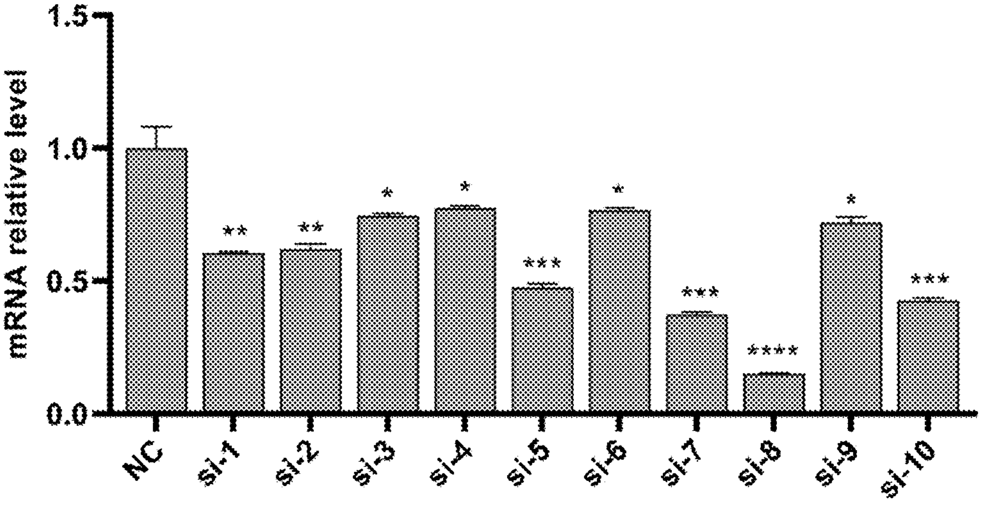
Figure 7C:
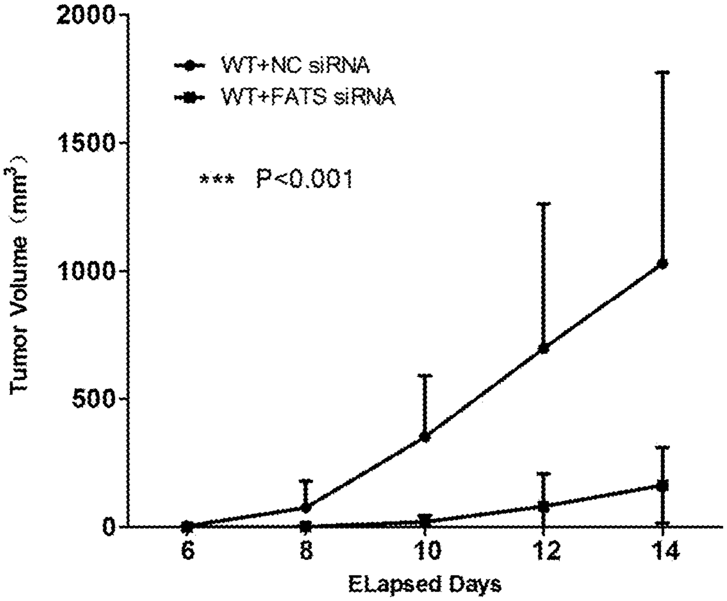

By using siRNA to silence the FATS in wild-type macrophages, FATS-siRNA and NC-siRNA were respectively transfected in wild-type macrophages, and subsequently these two transfected macrophages were respectively injected into the melanoma-bearing mice. As shown in FIGS. 7A-C, FATS-silenced macrophages could significantly inhibit the melanoma growth. Such results confirmed the therapeutic effect of FATS-deficient or silenced macrophages on the mouse melanoma.

Example 10 Effect of FATS-KO Mouse BM-Derived Macrophages on Apoptosis of Pancreatic Cancer Cells Isolation and directed differentiation of macrophages WT mice and FATS-deficient mice were sacrificed by cervical dislocation, and disinfected with 75% alcohol. The skin and muscles were stripped, and the limbs were collected with the residual muscles removed, and transferred to a Peri dish containing serum-free 1640 medium. Two ends of the bone were cut along the joint to expose the medullary cavity, and the bone marrow was flushed out with the serum-free 1640 medium by a 1 mL syringe until the bone turned white. Then the medium was pipetted to a 15 mL centrifuge tube, and centrifuged at 1,500 rpm for 7 min. The supernatant was discarded, and the cells were resuspended with a red blood cell lysis buffer, lysed on ice for 5 min, and added with PBS to terminate the lysis. The lysis product was centrifuged at 1,500 rpm for 7 min, and the supernatant was discarded. The cells were suspended with 10 mL PBS and centrifuged at 1,500 rpm for 7 min, and such process was repeated once. Then the cells were resuspended with 1 mL 1640 medium containing inactivated serum, and diluted 20 times for counting. The cell suspension was adjusted to a concentration of $5\times10^5$/mL with 1640 complete medium, added with M-CSF (100 μg/mL-20 ng/mL) and spread onto a 12-well plate for induction culture. 0.5 mL of the M-CSF-containing 1640 complete medium was replaced on the $3^{rd}$ day of the culture. IFN-γ (20 ng/mL) and LPS (100 ng/mL) were introduced on the $6^{th}$ day, and then 24 h differentiation into M1 macrophages were carried out.

Co-Culture of FATS-KO BM-Derived Macrophages and Panc02 Cells

Murine Panc02 cells were digested, and centrifuged at 1,000 rpm for 5 min. The supernatant was discarded, and the cells were suspended with 10 mL PBS, added with 20 μL cytoTell Blue solution and stained at 37° C. for 20 min. Then the cell suspension was centrifuged at 1,000 rpm for 5 min, and the supernatant was discarded. The cells were washed twice with PBS (10 mL for each), suspended with 1 mL 1640 medium, counted, and added to the 12-well plate containing the FATS-KO BM-derived macrophages, $2\times10^5$ Panc02 cells per well. The co-culture was performed for 24 hours.

Flow Cytometry Analysis of Cell Apoptosis

The co-culture system was washed twice with PBS (each for 0.5 mL), added with 200 μL 0.05% EDTA, and digested for 1 min. 600 μL of the 1640 complete medium was introduced to terminate the digestion, and the cells were pipetted and transferred to a flow cytometry tube. The tube was added with 1 mL PBS, and centrifuged at 1,500 for 7 min. The supernatant was discarded, and the cells were added with 1 mL PBS, mixed well with fingers, and centrifuged at 1,500 for 5 min. The supernatant was discarded, and such process was performed again. Each tube was added with 0.1 mL 1×binding buffer and mixed uniformly with fingers. Except for the blank group, each tube was added with 2.5 μL Annexin V-APC and 7-AAD, and the staining was performed at room temperature in the dark for 15 min.

After that, each tube was added with 0.2 mL 1×binding buffer and transferred to a flow cytometer for the detection of cell apoptosis.

Figure 8A:
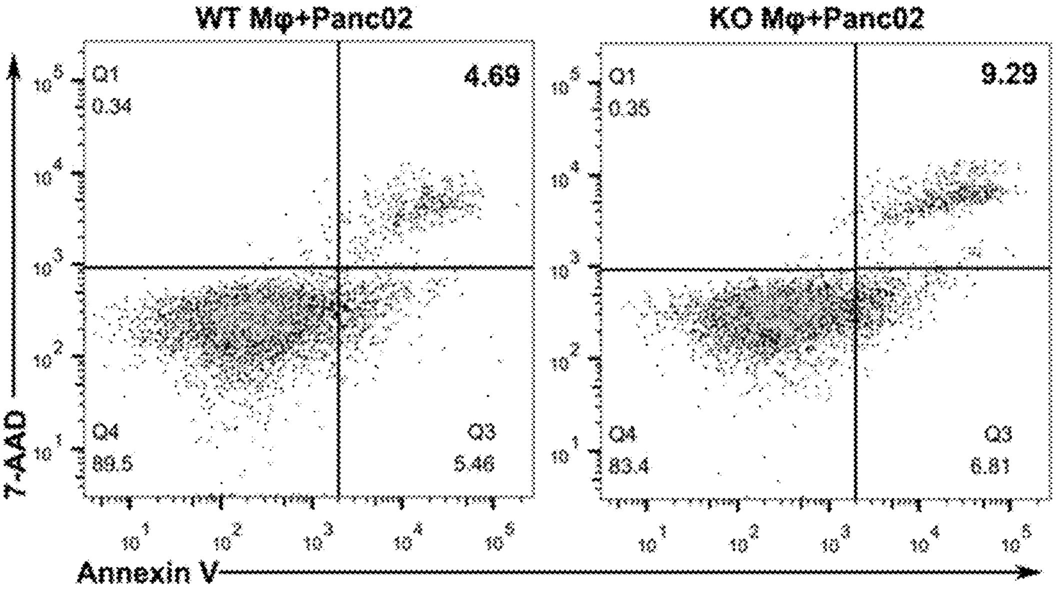
FIGS. 8A-B show flow cytometry analysis results for cell apoptosis, demonstrating that the FATS-KO macrophages can promote the apoptosis of panc02 cells (**, P<0.01).
Figure 8B:
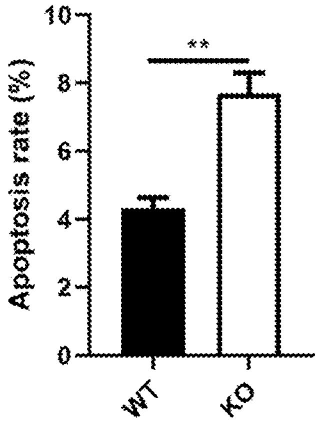

The flow cytometry analysis results were shown in FIGS. 8A-B. It can be observed that the FATS-KO macrophages could significantly promote the apoptosis of Panc02 cells.

The above experiments, analysis and discussion illustrated the correlation between FATS or its expression product and tumors or cancers. By detecting and analyzing the peripheral immune microenvironment of WT and FATS-KO mice, it was found that the frequency of $CD4^+$ T cells in the periphery increased, while the frequency of immunosuppressive Tregs decreased significantly; the frequency of $CD8^+$ T cells in the periphery had no significant increase, while the proportion of $CD44^{hi}$ in $CD8^+$ T cells increased significantly, indicating a significantly enhanced activity of $CD8^+$ T cells. Meanwhile, the changes of immune cells in the tumor immune microenvironment that played a key role in tumorigenesis and progression of tumors were analyzed, where it was observed that the frequency of total T cells in the tumor tissue and the frequency of $CD4^+$ T increased significantly, while the frequency of Treg cells did not alter significantly, indicating an increase in the frequency of Th1 cells. We also noticed an increase in CTL frequency in tumor tissue. The experimental results suggested the availability of FATS as a potential target for immunotherapy that can largely improve the therapeutic effect of immunotherapy by regulating the frequency and function of T cells in peripheral and tumor tissues.

In addition to antigen presentation and promotion of T-cell proliferation, M1 macrophages also played an important role in intrinsic immunity, since they can directly kill cells by producing NO. By comparison, M2 macrophages cannot produce NO, and thus no longer had a killing effect on cells. In other words, the knockout or inhibition of FATS can regulate the M1 polarization of macrophages, and increase and activate T cells, thereby inhibiting the tumor growth. Therefore, the knockout or inhibition of FATS can be applied to regulate M1 polarization of macrophages and increase and activate T cells.

Described above are merely preferred embodiments of the present disclosure, which are not intended to limit the disclosure. Any modification, replacement, improvement, etc., made by those skilled in the art without departing from the spirit and scope of the disclosure should also fall within the scope of the present disclosure defined by the appended claims.

---

What is claimed is:

1. A composition, comprising modified macrophages, wherein the modified macrophages have a deletion of fragile-site associated tumor suppressor (FATS) of SEQ ID NO: 1 or comprise a small interfering RNA (siRNA) capable of silencing the FATS of SEQ ID NO: 1, wherein the siRNA is SEQ ID NO:2.

2. The composition of claim 1, wherein the macrophages are bone marrow-derived macrophages (BMDMs).

3. The composition of claim 1, wherein the macrophages are M0 or M1 macrophages.

4. The composition of claim 1, wherein the macrophages are derived from an animal selected from the group consisting of a primate, a rodent and a pig.

5. A method for treating melanoma in a subject, comprising:

administering a therapeutically effective amount of the composition of claim 1 into the subject in need thereof, thereby treating the melanoma.

6. The method of claim 5, wherein the composition is administered via injection.

7. A method for treating melanoma in a subject, comprising:

a) introducing a small interfering RNA (siRNA) capable of silencing fragile-site associated tumor suppressor (FATS) of SEQ ID NO: 1 into macrophages to produce modified macrophages, wherein the siRNA is SEQ ID NO:2; and b) administering a therapeutically effective amount of a composition comprising the modified macrophages into the subject in need thereof, thereby treating the melanoma.

8. The method of claim 7, wherein in step a) the siRNA is introduced into the macrophages by transfection.

9. The method of claim 7, wherein in step b) the composition is administered via injection.

10. The method of claim 7, wherein the macrophages are bone marrow-derived macrophages (BMDMs).

11. The method of claim 7, wherein the macrophages are M0 or M1 macrophages.

12. The method of claim 7, wherein the macrophages are derived from an animal selected from the group consisting of a primate, a rodent and a pig.

13. A method for treating pancreatic cancer in a subject, comprising:

administering a therapeutically effective amount of a composition comprising modified macrophages into the subject in need thereof, thereby treating the pancreatic cancer, wherein the modified macrophages have a deletion of fragile-site associated tumor suppressor (FATS) of SEQ ID NO: 1.

14. The method of claim 13, wherein the composition is administered via injection.

15. The method of claim 13, wherein the macrophages are bone marrow-derived macrophages (BMDMs).

16. The method of claim 13, wherein the macrophages are M0 or M1 macrophages.

* * * * *